(12) United States Patent
Shang et al.

(10) Patent No.: US 8,206,652 B2
(45) Date of Patent: Jun. 26, 2012

(54) JET REACTOR WITH FLOW DUCTS AND PROCESS FOR PREPARING ISOCYANATES USING IT

(75) Inventors: Yonghua Shang, Yantai (CN); Zhongping Sun, Yantai (CN); Jianfeng Li, Yantai (CN); Yong Wang, Yantai (CN); Weiqi Hua, Yantai (CN); Deqiang Ma, Yantai (CN); Yongsheng Wang, Yantai (CN); Jiansheng Ding, Yantai (CN)

(73) Assignee: Ningbo Wanhua Polyurethanes Co., Ltd., Ningbo, Zhejiang Province (CN)

( * ) Notice: Subject to any disclaimer, the term of this patent is extended or adjusted under 35 U.S.C. 154(b) by 88 days.

(21) Appl. No.: 12/674,121

(22) PCT Filed: Aug. 21, 2007

(86) PCT No.: PCT/CN2007/002526
§ 371 (c)(1),
(2), (4) Date: Feb. 18, 2010

(87) PCT Pub. No.: WO2009/023989
PCT Pub. Date: Feb. 26, 2009

(65) Prior Publication Data
US 2011/0124907 A1  May 26, 2011

(51) Int. Cl.
*B01J 19/24* (2006.01)
*B01J 19/26* (2006.01)
*C07C 263/10* (2006.01)

(52) U.S. Cl. ..... 422/129; 422/224; 560/347; 366/165.1; 366/165.5

(58) Field of Classification Search ............ 422/129, 422/224; 560/347; 366/165.1, 165.5
See application file for complete search history.

(56) References Cited

U.S. PATENT DOCUMENTS

| 571,196 | A | * | 11/1896 | Kirkwood | 48/180.1 |
| 3,190,618 | A | * | 6/1965 | Katzen | 366/337 |
| 3,207,484 | A | * | 9/1965 | Rubin | 366/336 |
| 4,847,408 | A | | 7/1989 | Frosch et al. | 560/347 |
| 6,082,891 | A | | 7/2000 | Schubert et al. | 366/338 |

FOREIGN PATENT DOCUMENTS

| CN | 1034536 A | 8/1989 |
| CN | 1396152 A | 2/2003 |
| CN | 1496977 A | 5/2004 |
| DE | 10019414 A1 * | 10/2001 |
| EP | 0 289 840 | 4/1988 |

OTHER PUBLICATIONS

International Search Report from corresponding PCT/CN2007/002526 dated Jun. 12, 2008.

* cited by examiner

*Primary Examiner* — Jennifer A Leung
(74) *Attorney, Agent, or Firm* — Ohlandt, Greeley, Ruggiero, Perle, L.L.P.

(57) ABSTRACT

The present invention provides a flow duct type jet reactor and a process for preparing isocyanates using it. The flow duct type jet reactor situates flow ducts in inner feed pipe which form whirlpool and reinforce vortex, thereby amine steam rapidly admixes and reacts with phosgene, and the byproducts are reduced. In addition, the present process uses a jet-absorption apparatus which rapidly cools the high temperature gas discharged from the reactor to a temperature at which the product is thermally stable, and at the same time provides negative pressure for the reaction process of the system, and thus saving bulky vacuum system.

16 Claims, 2 Drawing Sheets

JET REACTOR WITH FLOW DUCTS AND PROCESS FOR PREPARING ISOCYANATES USING IT

CROSS-REFERENCE TO RELATED APPLICATION

This application is related to, and claims priority in, PCT Application No. PCT/CN2007/002526, filed on Aug. 21, 2007, is claimed under 35 U.S.C. §365, the disclosure of which is incorporated in its entirety by reference herein.

FIELD OF THE INVENTION

This invention relates to a jet reactor, especially to a flow duct type jet reactor, as well as to a process for preparing isocyanates using the reactor.

BACKGROUND OF THE INVENTION

As early as in 1940's, it has been reported of a gas-phase phosgenation for preparing isocyanates (Siefken, Annalen 562, 108, 1949). A gas-phase reaction is usually carried out in a tubular reactor. This phosgenation reaction is a fast process, which requires fast mixing rate and meanwhile needs to avoid blockage of the reactor at a high reaction temperature as possible. In the gas phase phosgenation at a high temperature, amines and isocyanates are extremely unstable to stay in a relatively long time at 300-500° C., which may cause decompositions like losing $NH_2$ or NCO groups and the like. Thus, on one hand, it needs to strengthen their mixing and reduce their residence time during the reaction process at a high temperature; on the other hand, it needs to conduct the reaction under negative pressure, especially for feedstocks of high boiling points, so as to make amines gasified at a relatively low temperature; furthermore, the obtained high temperature gas mixture needs to be quenched to about 140° C., so as to minimize the loss of products.

EP 0, 289, 840 discloses a cylindrical reactor without any moving parts inside. The reaction is carried out with reactant streams in a turbulent flow state. The gas phase phosgenation of aliphatic amines is a very fast reaction process determined by the mixing velocity. However, due to the back-mixing of reactants, isocyanates may react with amines to form solid by-products deposited on the surface of the reactor, which obstruct its gas flow channel.

U.S. Pat. No. 4,847,408 adopts a reactor where gaseous reactants are mixed and react under a strong turbulent flow state. The reactor has an inner diameter of 2.5 mm and a length of 17.5 mm. The stream of amines is rapidly ejected into the reactor via a nozzle. And HDI is obtained at 400° C. CN 1, 396, 152 improves the reactor described in U.S. Pat. No. 4,847,408 by converting the cylindrical reactor into a mixer of venturi-like in shape. This design may reduce back-mixing and the contact of the gaseous mixture with the inside wall of the reactor.

U.S. Pat. No. 6,082,891 describes a preparation of $H_6TDI$ using a microchannel mixer which shows a good result. However, a disadvantage of the reactor is that polymers produced and deposited at a high temperature may block the channel for its small size, and thereby the operation time has to be shortened.

EP 0, 289, 840 and U.S. Pat. No. 4,847,408 describe a condensation of products by absorbing them directly in a solvent. It needs a large solvent container and a big amount of solvents due to the short heat exchange time. Furthermore, quenching and absorption of the high temperature gas mixture may use a heat exchanger. By-products may deposit on surfaces of the heat exchanger, which impairs the heat transfer and finally leads to a blockage of the heat exchanger after a long term operation.

It can be seen from the above comparison that the phosgenation reaction of amines in the gas phase is a fast reaction process, which requires a higher mixing rate to avoid the production of by-products like ureas so as to avoid blockages. The key to obtain a good reaction result is to use a reactor having high mixing efficiency so as to reduce the production of solid by-products. Furthermore, quenching of a high temperature gas mixture also reduces the production of by-products. Therefore, there is a need to find an apparatus and a process for preparation of isocyanates, which provides rapid efficient mixing of reactants and quenching of the high temperature gas mixture after the reaction.

BRIEF DESCRIPTION OF THE INVENTION

The objective of the invention is to provide a flow duct type jet reactor, which can strengthen effect of turbulent flow and significantly improve the mixing effect of reactants so as to achieve the rapid mixing of reactants.

The flow duct type jet reactor of the invention comprises an internal feed tube, an external feed tube coaxial with the internal feed tube, and an annular space defined between the two feed tubes, wherein both ends of the external feed tube are closed; a reaction tube coaxially connected to the downstream of the internal feed tube; jet holes made in the wall of the downstream part of the internal feed tube and the jet holes are connected with flow ducts.

Wherein, said jet holes and said flow ducts are connected in a smooth transition manner. The outlets of flow ducts are positioned at a first suppositional circle which is coaxial with the internal feed tube, and the diameter of said first suppositional circle is 0.1 to 0.99 times of that of the internal feed tube, and preferably 0.4 to 0.9 times. The outlets of said flow ducts are preferably distributed on the same cross section of the internal feed tube, and more preferably symmetrically arranged at the first suppositional circle. Streams emerge from outlets of said flow ducts in a direction which is tangent with a second suppositional circle defined by the center of jet holes, the center of outlets of flow ducts and the axis of the internal feed tube, although deviations of this arrangement are feasible.

The cross section of jet holes and flow ducts may be in the shape of a circle, an oval, a square, a rhombus and the like. The flow ducts may be engineered to be a curve shape, and the curve is preferably overlapped with the second suppositional circle defined by the center of jet holes, the center of outlets of flow ducts and the axis of the internal tube.

The numbers of jet holes and flow ducts connected thereto are 2-20 respectively, preferably 3-15, more preferably 3-10, and most preferably 4-10. The total cross sectional area of all of jet holes or flow ducts is 2-30% of that of the internal feed tube, and preferably 5-15%.

Jet holes are arranged as close as possible to the bottom of the annular space defined by the internal feed tube and the external feed tube, and preferably they are not more than 10 cm away from the bottom.

A divergent channel is arranged at the downstream of said internal feed tube, and connected with a reaction tube. The angle between the wall of the divergent channel and the stream flow direction in the internal feed tube is 10-30 degrees. The inner diameter of the reaction tube is 1 to 2 times of that of the internal feed tube, and preferably 1.1 to 1.5 times.

All or parts of jet holes are arranged on the same cross section perpendicular to the stream flow direction in the internal feed tube, and symmetrically arranged over the wall of the internal feed tube, although deviations of this arrangement are feasible.

The reactor is generally made of steel, glass, alloy or enameled steel.

The external feed tube may be engineered with porous plates, baffle plates, packing layers and the like inside to stabilize reactant streams.

Another objective of the invention is to provide a process of a gas phase phosgenation for preparing isocyanates by using above described flow duct type jet reactors. More details are given as follows:

A process of a gas phase phosgenation for preparing aliphatic, alicyclic, or aromatic isocyanates having a general formula of $R(NCO)_n$ by using a above described flow duct type jet reactor, wherein R denotes an aliphatic, alicyclic, or aromatic hydrocarbon group with carbon atoms of 1 to 15, preferably 3 to 15, and more preferably 4 to 13; and the hydrocarbon group may contain heteroatoms such as O or S; and n is an integral number of 1-10, preferably 1-5, more preferably 2-4 and most preferably 2 or 3; said process comprises the following steps:

(a) an amine having a general formula of $R(NH_2)_n$ and phosgene are heated respectively to 120° C.-500° C. to be gasified, wherein R and n are defined as above;

(b) phosgene enters and flows parallelly through the internal feed tube of the reactor, and the amine in vapor form enters the external feed tube via its inlet and then is ejected to the internal feed tube via jet holes and flow ducts;

(c) phosgene and the amine vapor are mixed and enter the reaction tube to react.

Wherein, in step (a), the amine may optionally be diluted with an inert gas or with the vapors of an inert solvent. The inert gas may be selected from nitrogen or argon gas and the like, and the inert solvent may be selected from toluene, xylene, chlorobenzene, o-dichlorobenzene or decalin and the like. In step (a), the amine and phosgene are usually heated to 120° C.-500° C. respectively, and preferably 250° C.-400° C. Based on the mole quantity of amino group, phosgene usually exceeds 25%-350%, and preferably 50%-250%, and the use amount of the inert gas or the inert solvent is usually 0.1-2 times of the mole of amino groups, and preferably 0.2-1 times.

Wherein, in step (b), the average velocity of the amine vapor through all of jet holes and flow ducts is 6 to 120 m/s, and the average velocity of phosgene through the phosgene feed tube is 3 to 20 m/s. The ratio of the velocity of the amine vapor at the outlets of flow ducts to phosgene is 1:1 to 10:1, and preferably 3:1 to 5:1.

The amines used in the invention are primary amines which can turn to a gas form without decomposition. Suitable amines are aliphatic, alicyclic or aromatic mono-amines, diamines, triamines, tetramines or pentamines and the like having carbon atoms of 1-15, preferably 3-15, and more preferably 4-13. For example, suitable aliphatic diamines include 1,4-diaminobutane, 1,6-diaminohexane, 1,4-diaminocyclohexane, 1-amino-3,3,5-trimethyl-5-aminomethyl-cyclohexane (IPDA), 4,4'-diaminodicyclohexylmethane ($H_{12}$MDA) and the like. Suitable aliphatic triamines include 4-(aminomethyl)octane-1,8-diamine, triaminononane and the like. Preferred amines are 1,6-diaminohexane, IPDA, $H_{12}$MDA and triaminononane. Suitable aromatic amines include 2,4-/2,6-toluene diamines with an isomer ratio of 80/20 to 65/35, 2,4-toluene diamines (TDA), diaminobenzene, naphthalenediamine, 2,4'-/4,4'-diamino diphenyl methane and the isomer mixture thereof. The amine may also be an amine containing heteroatoms, like 2-tetrahydrofurfurylamine.

The diamine is preferably 4,4'-diaminodicyclohexylmethane, 1-amino-3,3,5-trimethyl-5-aminomethyl-cyclohexane (IPDA), or 1,6-diaminohexane. the triamine is preferably triamino nonane.

During the phosgenation of step (c), the pressure (absolute pressure) in feed tubes is preferably 200 to 3000 mbar, and the outlet pressure of the reaction tube of the reactor is preferably 150 to 1500 mbar. The velocity of phosgene prior to the mixing is at least 1 m/s, and preferably 3-20 m/s; the velocity of the amine vapor at the outlets of jet holes is usually 6-120 m/s, and preferably 20-100 m/s.

Wherein, the process further comprises step (d): the high temperature gas mixture emerging from the reaction tube is quenched.

In step (d), the high temperature gas mixture is quenched by a jet-absorption apparatus, which comprises a liquid-gas jet absorber, a circulation pump, and an absorption trough. An absorption solution in the absorption trough is pressured by the circulation pump, and then ejected to the jet absorber via a nozzle of the liquid-gas jet absorber; the high temperature gas mixture is rapidly sucked into the jet absorber due to the negative pressure brought by the high speed flow of the solution, so as to achieve sufficient mixing of the solution and the gas mixture, and then quenching. The reaction product in the absorption trough is further collected and absorbed by a liquid solvent. And then, after pressured by the circulation pump, one part of the absorption solution is transmitted to a phosgenation solution post-process system for solvent removement and purification, and the other part is combined with supplementing fresh solvent and transmitted to the jet absorber for quenching and absorption of the high temperature gas mixture.

A packing tower is preferred to be set at the top of the jet absorber, and a part of the absorption solution is transmitted to the top of the packing tower after pressured by the circulation pump, so as to further absorb the unabsorbed gas mixture in the jet absorber. More preferably, the packing tower is connected with a condenser wherein gas in the packing tower is further condensed by the condenser (cooling medium is water), and incondensable gas is transmitted to a HCl and $COCl_2$ recycle device so as to improve the post treatment efficiency of the phosgenation solution.

In step (d), the absorption solution in the absorption trough has a temperature in a range of 130-150° C., and may be selected from pure solvents including toluene, xylene, chlorobenzene or o-dichlorobenzene, or a mixture of any of the foregoing solvents with 5 wt %-50 wt % of aliphatic, alicyclic or aromatic isocyanates of $R(NCO)_n$. The temperature of the absorption solution prior to the ejection to the jet absorber is 80° C.-120° C.

In step (d), the liquid-gas jet absorber may be a venturi-like type one, a rotating jet with long pipes, or a multi-nozzle jet. The jet absorber may be single stage or multi-stage. A static mixer is preferred to be set at the outlet of the jet absorber. Approaches to improve the absorption effect of the jet absorber are not limited to the set forth ones.

Wherein, the high speed ejection of the solution inside the jet absorber may provide a vacuum of 0 mbar to −700 mbar to the reaction system, and preferably −200 mbar to −500 mbar. The vacuum is produced by controlling the velocity and the pressure head of the circulation pump. According to the reaction gas flow rate, the flow rate in the circulation pump is 20 liters/s-1000 liters/s, and the gauge pressure of the circulation pump is preferred to be 3 bars to 30 bars.

The isocyanates of the invention may be selected from any of the following compounds: 1,4-butanediisocyanate, 1,6-hexamethylene diisocyanate, 1,4-cyclohexanediisocyanate, isophorone diisocyanate (IPDI), dicyclohexylmethane-4,4'-diisocyanate ($H_{12}MDI$), nonane triisocyanate, or toluene-2, 4-diisocyanate (TDI).

The advantages of setting certain number of flow ducts at suitable positions in the internal feed tube are to achieve the mixing of two components at any position, and to form whirls under the direction effect and reinforce vortex, so as to ensure the amine vapor and phosgene are rapidly mixed and react and to minimize the production of by-products. Besides, the jet absorber used in the invention quenches the high temperature gas mixture emerging from the reaction tube to a temperature at which products are stable, and meanwhile produces negative pressure for the reaction system. The phosgenation product flows to the jet absorber fast under negative pressure so as to ensure the phosgenation product is absorbed, and quenched fast and efficiently. The gas jet-absorption apparatus used in the invention has a relatively larger volume flow ratio of liquid-gas, stronger absorption intensity and more powerful process ability and provides negative pressure to the reaction tube which is more suitable for the phosgenation under negative pressure, so as to save bulky vacuum system and avoid decomposition of amines.

DETAILED DESCRIPTION OF THE INVENTION AND EMBODIMENTS

The jet-reactor of the present invention will be described in detail with the accompanying drawings and embodiments, but not limited to these embodiments and examples.

Figure 1:
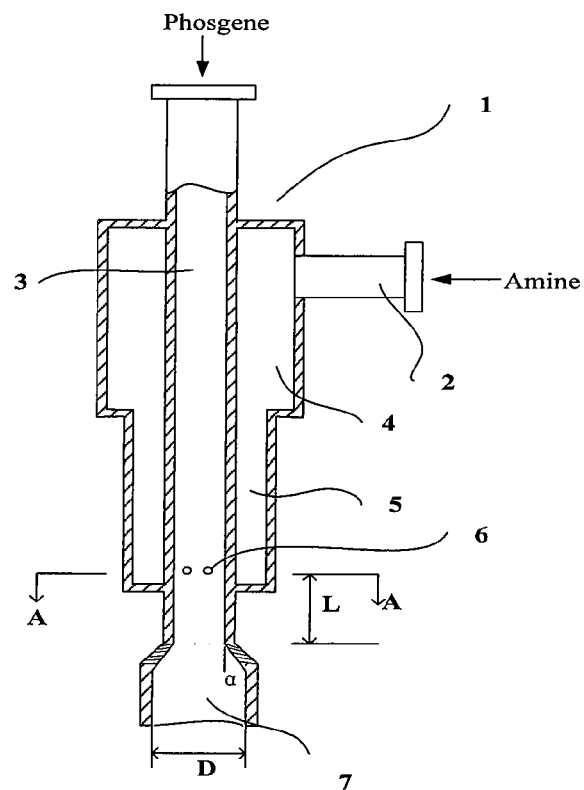
FIG. 1 shows a longitudinal section view through one embodiment of the flow duct type jet reactor of the invention.

FIG. 1 shows a flow duct type jet reactor 1 of the invention, comprising: an internal feed tube 3, an external feed tube 4 coaxial with the internal feed tube 3, and an annular space 5 defined between the two feed tubes, wherein both ends of the external feed tube are closed; a reaction tube 7 coaxially connected to the downstream of the internal feed tube; jet holes 6 made in the wall of the downstream part of the internal feed tube 3 and the jet holes 6 are connected with flow ducts 8.

According to the reactor of the present invention, the external feed tube 4 is engineered inside with porous plates, baffle plates, or packing layers and the like to stabilize reactant streams. There is no specific requirement on the space thickness of the annular space 5, and the space thickness of the annular space 5 is usually 0.1 to 0.8 times of the inner diameter of the internal feed tube, preferably 0.2 to 0.6 times and more preferably 0.2 to 0.4 times. A divergent channel can be understood as a channel with its cross section gradually increasing along the stream flow direction. The inner diameter D of the reaction tube 7 is larger than the inner diameter of the internal feed tube 3, and generally the inner diameter D of the reaction tube is 1 to 2 times of the inner diameter of the internal feed tube, and preferably 1.1 to 1.5 times. The angle α between the divergent channel and the stream flow direction in the internal feed tube is 10-30 degrees. The number of jet holes 6 is 2-20, preferably 3-15, and more preferably 3-10.

The total cross sectional area of all of jet holes 6 or flow ducts 8 is 2-30% of that of the internal feed tube, and preferably 5-15%.

Figure 2:
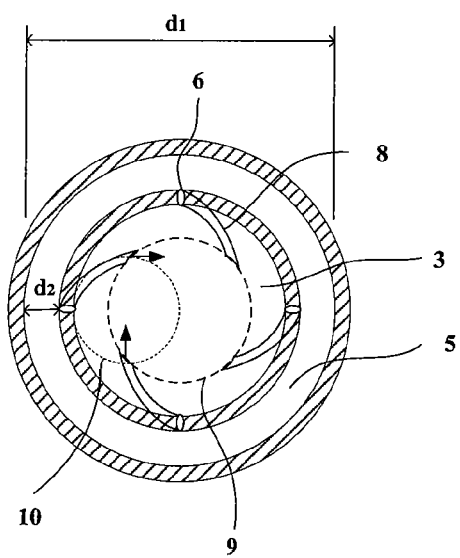
FIG. 2 is an enlarged view of the cross section along line A-A of FIG. 1.

FIG. 2 is an enlarged view of cross section along the line A-A of FIG. 1. In one preferred embodiment, four flow ducts 8 are arranged in the internal feed tube 3, and jet holes 6 are symmetrically arranged on the same cross section over the internal feed tube. The number of flow ducts is 4. The outlets of all of flow ducts 8 are positioned at a first suppositional circle 9, and the first suppositional circle is co-axial with the phosgene feed tube. The diameter of the first suppositional circle 9 is 0.1 to 0.99 times of the inner diameter of the internal feed tube, and preferably 0.4-0.9 times. The outlets of flow ducts 8 are preferably symmetrically arranged on the first suppositional circle 9, and preferably on the same cross section. The flow ducts 8 are engineered to be a curve shape, and the curve is overlapped with a second suppositional circle 10 defined by the center of jet holes, the center of outlets of flow ducts and the axis of the internal tube. The instantaneous flow direction of the amine vapor at the outlet of a single flow duct is preferred to be tangent with the second suppositional circle 10. The proper arrangement of flow ducts achieves that the amine streams from four flow duct outlets form whirlpool under the direction effect and reinforce vortex so as to make amines and phosgene mixed and react fast.

The phosgenation reaction is conducted in the above-described reactor, the amine vapor diluted with an inert gas or with an inert solvent vapor enters the external feed tube 4 via its inlet 2, flows through the annular space 5 and jet holes 6 in the wall of the internal feed tube 3 to flow ducts 8 and then is ejected to the phosgene stream. The phosgene stream flows directly through the internal feed tube 3 to the reactor 1. Under the direction effect of flow ducts 8, several amine streams from flow ducts 8 form whirlpool and reinforce vortex, and usually they are mixed with phosgene in a strong turbulent flow state and then enters a reaction tube 7 via a divergent channel with the reaction continued to obtain a high temperature gas mixture of corresponding isocyanates, phosgene and so on. The high temperature gas mixture then flows into a gas jet-absorption apparatus for quenching and absorption to obtain desired phosgenation solution.

Prior to the phosgenation reaction, the amine is generally heated to 120° C.-500° C., and preferably 250° C.-400° C., and the amine vapor is usually diluted with an inert gas like nitrogen or argon or with an inert solvent vapor of toluene, xylene, chlorobenzene, o-dichlorobenzene or decalin; the phosgene is generally heated to 120° C.-500° C., and preferably 250° C.-400° C. Based on the mole quantity of amino group, phosgene exceeds 25%-350%, and preferably 50%-250%, and the use amount of the inert gas or the inert solvent is usually 0.1-2 times of the mole of amino groups, and preferably 0.2-1 times.

During the phosgenation reaction, the pressure (absolute pressure) in feed tubes is preferably 200 to 3000 mbar, and the outlet pressure of the reaction tube of the reactor is preferably 150 to 1500 mbar. The velocity of phosgene prior to the mixing is at least 1 m/s, and preferably 3-20 m/s; the velocity of the amine vapor at the outlets of jet holes is usually 6-120 m/s, and preferably 20-100 m/s.

Figure 3:
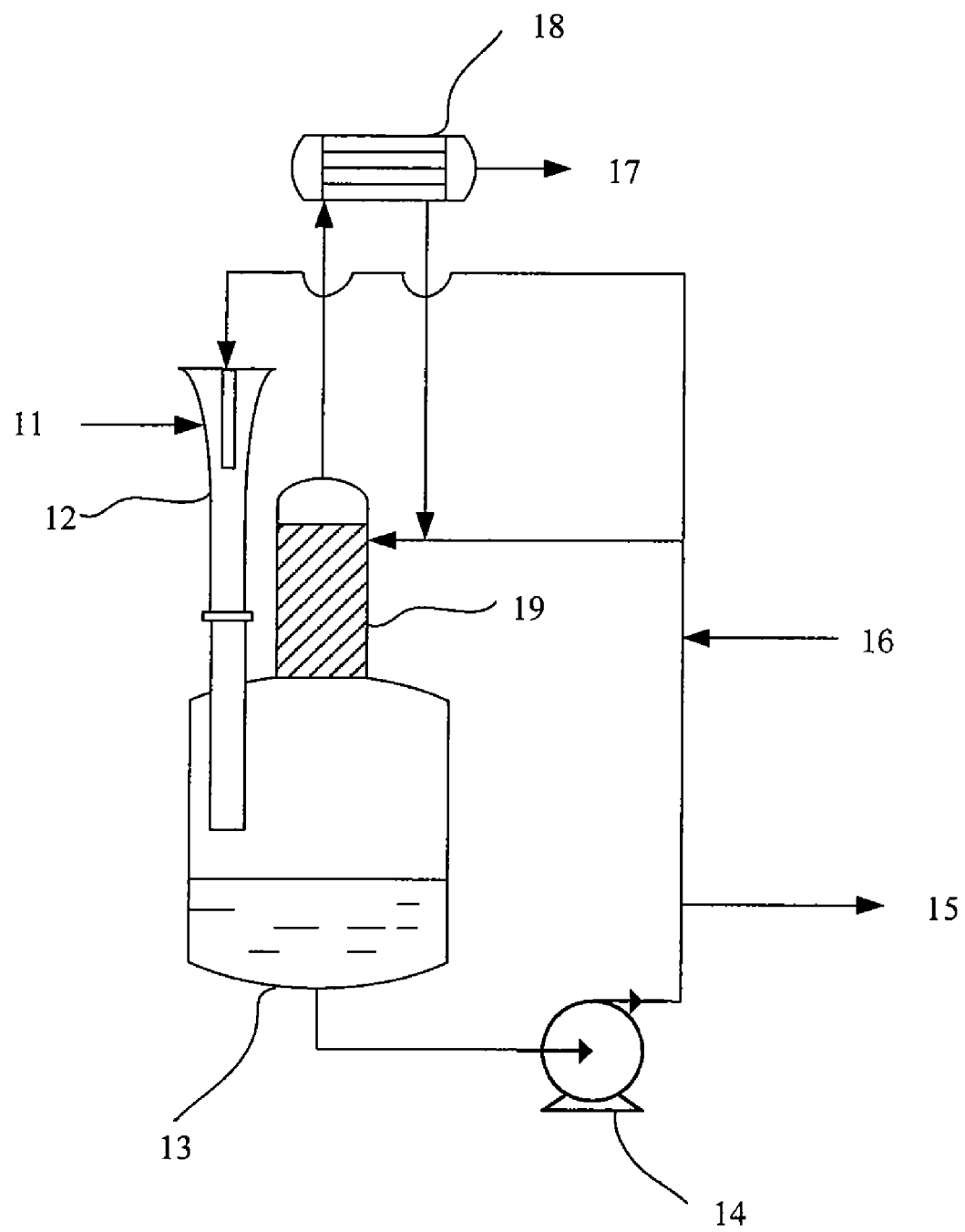
FIG. 3 shows one preferred embodiment of the gas jet-absorption apparatus used in the invention.

FIG. 3 shows a preferred embodiment of the gas jet-absorption apparatus used in the invention. After the phosgenation in the reaction tube 7, the high temperature gas mixture flows into a jet-absorption apparatus for quenching. An absorption solution is pressured by a circulation pump 14, and then ejected to the jet absorber via a nozzle of the jet absorber 12; the high temperature gas mixture is rapidly sucked into the jet absorber due to the negative pressure brought by the high speed flow of the solution, so as to achieve sufficient mixing of the solution and the gas mixture, and then quenching; the reaction product in an absorption trough 13 is further collected and absorbed by a liquid solvent. One part of the absorption solution in the absorption trough is transmitted via the circulation pump 14 to a phosgenation solution post-process system 15 for solvent removement and purification, another part is transmitted to the top of a packing tower 19 to wash the gas in the absorption trough 13, and the third part is transmitted to the jet absorber 12 for quenching and absorption of the high temperature gas mixture with a supplementing fresh solvent 16 together. The gas phase after going through the packing washing layer is further condensed in a condenser 18 (cooling medium is water), wherein partial solvent and products in the gas phase flow into the condenser 18 at atmospheric pressure, and incondensable gas is transmitted to a HCl and $COCl_2$ recycle device 17 so as to improve the post-treatment efficiency of phosgenation solution.

EXAMPLE 1

4,4'-diaminodicyclohexylmethane (HMDA), phosgene and nitrogen, in a mole ratio of 1:4:1, continuously flow to their corresponding feed tubes respectively. The downstream part of the reactor is connected with a gas jet absorption apparatus (for quenching) and an absorption tower for excess phosgene and hydrochloride. HMDA, phosgene and nitrogen are preheated to 360° C. prior to entering the reactor shown in FIG. 1. The HMDA vapor is diluted with an equivalent amount of nitrogen by the mole of the HMDA to form a mixture, and then the mixture flows into flow ducts via six lateral holes in the internal feed tube; the inner diameters of lateral holes and flow ducts are 1.5 mm, the inner diameter of the internal feed tube is 12 mm, the inner diameter of the external feed tube is 30 mm, the inner diameter of the annular space 5 is 20 mm, the distance between lateral holes and the bottom of the annular space is 1 cm, the distance L from lateral holes to the starting point of the divergent channel is 5 cm, the angel α between the divergent channel and the stream flow direction in the internal feed tube is 20 degrees, and the inner diameter D of the reaction tube is 15 mm. The instantaneous flow direction of the amine vapor at the outlet of a single flow duct is tangent with a second suppositional circle defined by the center of jet holes, the center of outlets of flow ducts and the axis of the phosgene feed tube, and the diameter of the first suppositional circle is 0.65 times of the inner diameter of the internal feed tube.

The vacuum in the reaction tube is maintained at −400 mbar by the sucking effect of high speed liquid in the gas jet absorption apparatus (a complex vacuum system and cost are saved). Wherein, the velocity of the mixture of the amine vapor and nitrogen through flow ducts is about 38 m/s, and the velocity of phosgene prior to the mixing is about 8 m/s. After emerging from the reaction tube of the reactor, the reaction product HMDI is quenched to 140° C. to 150° C. by a gas jet absorption apparatus with an o-dichlorobenzene solution of HMDI to obtain a phosgenation solution, and the o-dichlorobenzene solution is at 120° C. The GC assay indicates that the content of HMDI in the phosgenation solution is 99.24% (normalization), and the yield of HMDI is 97.9% of the theory yield.

COMPARATIVE EXAMPLE 1-1

Example 1 is repeated under the same conditions, but the flow duct type jet reactor is replaced by a central nozzle type jet comprising a central nozzle and an annular space wherein the cross sectional area of the central nozzle equals to the total cross sectional area of flow ducts, the area of the annular space between the central nozzle and the wall of the cylindrical reactor equals to the cross sectional area of the phosgene feed tube in Example 1 and the area of the reaction tube connected to the bottom of the mixer equals to that of the reaction tube in Example 1. In this central nozzle type reactor, a mixture of the amine vapor and nitrogen flows through the central nozzle, and phosgene flows through the annular space. The GC assay indicates that the content of HMDI in the phosgenation solution is 99.08% (normalization), and the yield of HMDI is 97.4% of the theory yield.

COMPARATIVE EXAMPLE 1-2

The gas jet absorption apparatus is replaced by a solvent absorption tower to quench the high temperature gas mixture (which needs a complex vacuum system and an additional cooling system), and the rest is the same as Example 1. The yield of HMDI is 97.6% of the theory yield. It shows that the yield is relatively lower and the system is more complex by comparison.

EXAMPLE 2

4,4'-diaminodicyclohexylmethane (HMDA), phosgene and nitrogen, in a mole ratio of 1:4:1, continuously flow to their corresponding feed tubes of the reactor shown in FIG. 1 respectively. HMDA, phosgene and nitrogen are preheated to 360° C. prior to entering the reactor shown in FIG. 1. A reactor similar to one in Example 1 is used, the HMDA vapor and nitrogen flows into flow ducts via four lateral holes in the internal feed tube; inner diameters of lateral holes and flow ducts are 2.0 mm, the inner diameter of the internal feed tube is 12 mm, the diameter of a first suppositional circle is 0.7 times of that of the internal feed tube and the rest parameters are the same as those in Example 1. The vacuum in the reaction tube is −400 mbar, the velocity of the mixture of the amine vapor and nitrogen through flow ducts is about 34 m/s, and the velocity of phosgene prior to the mixing is about 8 m/s. After emerging from the reaction tube of the reactor, the reaction product HMDI is quenched to 140° C. to 150° C. by a gas jet absorption apparatus with an o-dichlorobenzene solution of HMDI to obtain a phosgenation solution, and the o-dichlorobenzene solution is at 120° C. The yield of HMDI is 97.8% of the theory yield.

EXAMPLE 3

Isophoronediamine (IPDA), phosgene and nitrogen, in a mole ratio of 1:4:1, continuously flow to the same reactor as one in Example 1. Prior to entering the reactor, IPDA, phosgene and nitrogen are separately preheated to 320° C. Under nearly the same reaction conditions, the yield of obtained IPDI is 98.8% of the theory.

What are claimed are:

1. A jet reactor, comprising: an internal feed tube, an external feed tube coaxial with the internal feed tube, and an annular space defined between two said feed tubes, wherein both ends of the external feed tube are closed; a reaction tube coaxially connected to the downstream of the internal feed tube, jet holes made in the wall of the downstream part of the internal feed tube and the jet holes are connected with flow ducts, wherein said jet holes and said flow ducts are connected in a smooth transition manner, and the numbers of said jet holes and said flow ducts connected thereto are 2-20 respectively, wherein outlets of flow ducts are positioned at a first suppositional circle coaxial with the internal feed tube and symmetrically arranged at the first suppositional circle, and the diameter of said first suppositional circle is 0.1 to 0.99 times of the inner diameter of the internal feed tube, wherein the flow direction of a feedstock at outlets of flow ducts is tangent with a second suppositional circle defined by the center of jet holes, the center of outlets of flow ducts and the axis of the internal feed tube; and wherein flow ducts are engineered to be a curve shape, and the curve shape is overlapped with the second suppositional circle.

2. The jet reactor according to claim 1, wherein, the total cross sectional area of all of jet holes or flow ducts is 2-30% of that of the internal feed tube; said jet holes are arranged as close as possible to the bottom of the annular space defined by the internal feed tube and the external feed tube.

3. The jet reactor according to claim 2, wherein, all or parts of said jet holes are arranged on the same cross section of the internal feed tube, and symmetrically arranged in the wall of the internal feed tube; said jet holes are positioned not more than 10 cm away from the bottom of the annular space; outlets of said flow ducts are positioned on the same cross section of the internal feed tube.

4. The jet reactor according to claim 3, wherein, a divergent channel is arranged at the downstream of said internal feed tube, and connected with a reaction tube; the inner diameter of the reaction tube is 1 to 2 times of that of the internal feed tube; the distance from said jet holes to the starting point of the divergent channel is 1-15 times of the diameter of the internal feed tube, and the angle between the divergent channel and the stream flow direction in the internal feed tube is 10-30 degrees.

5. The jet reactor according to claim 4, wherein, the external feed tube has porous plates, baffle plates, or packing layers inside.

6. The jet reactor according to claim 5, wherein, the number of flow ducts is 3-10; the diameter of said first suppositional circle is 0.4 to 0.9 times of the inner diameter of the internal feed tube; the total cross sectional area of all of said jet holes or said flow ducts is 5-15% of that of the internal feed tube; the distance from said jet holes to the starting point of the divergent channel is 3-6 times of the diameter of the internal feed tube.

7. A process of a gas phase phosgenation for preparing aliphatic, alicyclic, or aromatic isocyanates having a general formula of $R(NCO)_n$ by using the jet reactor according to claim 1, wherein R denotes an aliphatic, alicyclic, or aromatic hydrocarbon group with carbon atoms of 1 to 15 and n is an integral number of 1-10, and said process comprises the following steps:

(a) an amine having a general formula of $R(NH_2)_n$ and phosgene are heated respectively to 120° C.-500° C. to be gasified, wherein R and n are defined as above;

(b) phosgene enters and flows parallelly through the internal feed tube of the reactor, and the amine vapor enters the external feed tube via its inlet and then is ejected to the internal feed tube via the jet holes and the flow ducts; and (c) phosgene and the amine vapor are mixed and enter the reaction tube to react.

8. The process according to claim 7, wherein, the process further comprises step (d): the high temperature gas mixture emerging from the reaction tube is quenched.

9. The process according to claim 8, wherein, in step (d), the high temperature gas mixture is quenched by a jet-absorption apparatus comprising a liquid-gas jet absorber, a circulation pump and an absorption trough.

10. The process according to claim 9, wherein, the average velocity of said amine vapor through all of the jet holes and the flow ducts is 6 to 120 m/s; and the average velocity of phosgene through the internal feed tube is 3 to 20 m/s; and the velocity ratio of the amine vapor at the outlets of the flow ducts to phosgene is 1:1 to 10:1.

11. The process according to claim 10, wherein, in step (a), the amine vapor is diluted with an inert gas or with an inert solvent vapor; wherein the inert gas is selected from nitrogen or argon; and the inert solvent vapor is selected from toluene, xylene, chlorobenzene, o-dichlorobenzene or decalin.

12. The process according to claim 11, wherein, during the phosgenation of step (c), the absolute pressure in the feed tubes is 200-3000 mbar; and the outlet pressure of the reaction tube of the reactor is 150-1500 mbar; and the velocity of the amine vapor at the outlets of the jet holes is 6-120 m/s.

13. The process according to claim 12, wherein, in step (d), the absorption solution in the absorption trough has a temperature of 130-150° C., and is selected from pure solvents including toluene, xylene, chlorobenzene or o-dichlorobenzene, or a mixture of any of the foregoing solvents with 5 wt%-50 wt% of aliphatic, alicyclic or aromatic isocyanates of $R(NCO)_n$.

14. The process according to claim 13, wherein, in step (d), the liquid-gas jet absorber is a venturi jet absorber, a rotating jet absorber with elongated pipes, or a multi-nozzle jet absorber; the jet absorber is single stage or multi-stage; a static mixer is set at the outlet of the jet absorber; and the high speed ejection of liquids inside the jet absorber provides a vacuum of 0 mbar to -700 mbar to the reaction system.

15. The process according to claim 14, wherein, the isocyanate is selected from any of the following chemicals: 1,4-butanediisocyanate, 1,6-hexamethylene diisocyanate, 1,4-cyclohexanediisocyanate, isophorone diisocyanate, dicyclohexylmethane-4,4'-diisocyanate, nonane triisocyanate, or toluene-2,4-diisocyanate.

16. The process according to claim 14, wherein, the amine having a general formula of $R(NH_2)_n$ is selected from any of the following chemicals: 1,4-diaminobutane, 1,6-diaminohexane, 1,4-diaminocyclohexane, 1-amino-3,3,5-trimethyl-5-aminomethyl-cyclohexane, 4,4'-diaminodicyclohexylmethane, triamino nonane, a mixture of 2,4-/2,6-toluene diamines with an isomer ratio of 80/20-65/35, or pure 2,4-toluene diamine.

* * * * *